(12) United States Patent
Pickar et al.

(10) Patent No.: US 6,583,170 B1
(45) Date of Patent: Jun. 24, 2003

(54) 2-PHENYL-1-[4-(AMINO-1-YL-ALK-1-YNYL)-BENZYL]-1H-INDOL-5-OL AND ESTROGEN FORMULATIONS

(75) Inventors: James Harrison Pickar, Springfield, PA (US); Barry Samuel Komm, Havertown, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/306,045

(22) Filed: May 6, 1999

Related U.S. Application Data

(60) Provisional application No. 60/108,156, filed on May 15, 1998.

(51) Int. Cl.[7] .................. A61K 31/40; A61K 31/405; A61K 31/56
(52) U.S. Cl. .................. 514/421; 415/426; 415/182
(58) Field of Search .................. 514/323, 339, 514/253, 415, 421, 426, 182

(56) References Cited

U.S. PATENT DOCUMENTS 5,880,137 A * 3/1999 Miller et al. .................. 514/323

* cited by examiner

*Primary Examiner*—Theodore J. Criares
(74) *Attorney, Agent, or Firm*—Arnold S. Milowsky

(57) ABSTRACT

The present invention relates to new formulations containing one or more estrogens and 2-Phenyl-1-[4-(amino-1-yl-alk-1-ynyl)-benzyl]-1H-indol-5-ol compounds which are useful as estrogenic agents, as well as pharmaceutical compositions and methods of treatment utilizing these compounds, which have the general structure below:

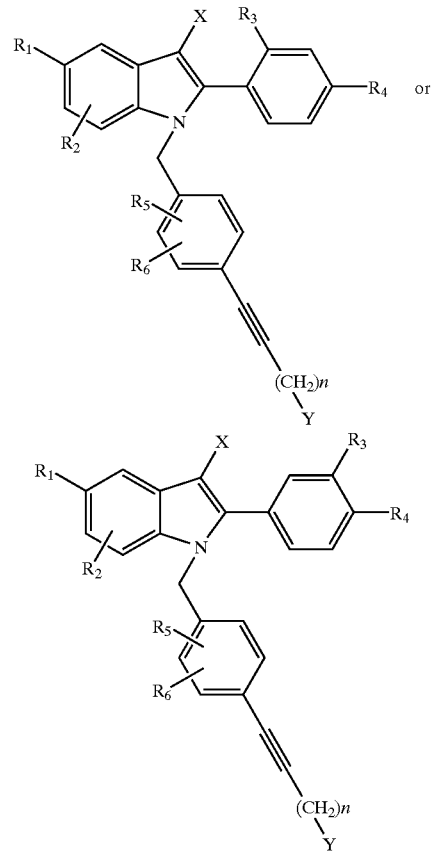

and related methods of treatment for providing tissue selective estrogenic activity while minimizing undesirable side effects of estrogen treatment or therapy, such as excessive estrogenic uterine stimulation.

2 Claims, No Drawings

2-PHENYL-1-[4-(AMINO-1-YL-ALK-1-YNYL)-BENZYL]-1H-INDOL-5-OL AND ESTROGEN FORMULATIONS

This application claims the benefit of U.S. Provisional Application No. 60/108,156, which was converted from U.S. patent application Ser. No.09/079,604, filed May 15, 1998, pursuant to a petition filed under 37 C.F.R. 1.53(c)(2)(i) now abandoned.

The present invention relates to the use of new 2-Phenyl-1-[4-(amino-1-yl-alk-1-ynyl)-benzyl]-1H-indol-5-ol compounds which are useful as selective estrogen receptor modulating agents, in conjunction with estrogens, as well as pharmaceutical compositions and methods of treatment utilizing these compounds.

BACKGROUND OF THE INVENTION

The use of hormone replacement therapy for bone loss prevention in post-menopausal women is well precedented. The normal protocol calls for estrogen supplementation using such formulations containing estrone, estriol, ethynyl estradiol, 17β-estradiol, esterified estrogens, or conjugated estrogens isolated from natural sources (i.e. Premarin® conjugated estrogens from Wyeth-Ayerst) or synthetic estrogens. In some patients, therapy may be contraindicated due to the proliferative effects of unopposed estrogens (estrogens not given in combination with progestins) have on uterine tissue. This proliferation is associated with increased risk for endometriosis and/or endometrial cancer. The effects of unopposed estrogens on breast tissue are less clear, but are of some concern. The need for estrogens which can maintain the bone sparing effect while minimizing the proliferative effects in the uterus and breast is evident. Certain nonsteroidal antiestrogens have been shown to maintain bone mass in the ovariectomized rat model as well as in human clinical trials. Tamoxifen (sold as Novadex® brand tamoxifen citrate by Zeneca Pharmaceuticals, Wilmington, Del.), for example, is a useful palliative for the treatment of breast cancer and has been demonstrated to exert an estrogen agonist-like effect on the bone, in humans. However, it is also a partial agonist in the uterus and this is cause for some concern. Raloxifene, a benzothiophene antiestrogen, has been shown to stimulate uterine growth in the ovariectomized rat to a lesser extent than Tamoxifen while maintaining the ability to spare bone. A suitable review of tissue selective estrogens is seen in the article "Tissue-Selective Actions Of Estrogen Analogs", *Bone* Vol. 17, No. 4, October 1995, 181S–190S.

The use of indoles as estrogen antagonists has been reported by Von Angerer, Chemical Abstracts, Vol. 99, No. 7 (1983), Abstract No. 53886u. Also, see, J.Med.Chem. 1990, 33, 2635–2640; J.Med.Chem. 1987, 30, 131–136. Also see Ger. Offen., DE 3821148 A1 891228 and WO 96/03375. These prior art compounds share structural similarities with the present compounds, but are functionally different. For compounds containing a basic amine, there is no phenyl group to rigidify the side chain.

WO A 95 17383 (Karo Bio AB) describes indole antiestrogens with long straight chains. Another related patent WO A 93 10741 describes 5-Hydroxyindoles with a broad range of side chains. WO 93/23374 (Otsuka Pharmaceuticals, Japan) describes compounds sharing structural similarities with those of the present invention, except with the structure referred to as $R_3$ in the present formulas I and II, below, is defined as thioalkyl and the reference discloses no such compounds having chains from the indole nitrogen having the same structure as the ones provided by the present invention.

In their article *Postmenopausal Hormone replacement therapy with estrogen periodically supplemented with antiestrogen*, Am. J. Obstet. Gynecol., Vol. 140, No. 7, 1981, pp. 787–792, Kauppila et al. describe their study of postmenopausal estrogen therapy of seven-week estrogen regimens followed by 10-day treatments with the antiestrogen clomiphene citrate.

Also, in their article *Comparison of Megestrol Acetate and Clomiphene Citrate as Supplemental Medication in Posmenopausal Oestrogen Replacement Therapy*, Arch. Gynecol. (1983) 234:49–58, Kauppila et al. describe combination therapies in postmenopausal women of estrogen with random supplementation of megestrol acetate or clomiphene citrate.

U.S. Pat. No. 4,894,373 (Young) teaches the use of antiestrogens, including clomiphene and its isomers, citrates and derivatives, in the absence of estrogen for treating menopausal symptoms and treating or preventing osteoporosis. U.S. Pat. No. 5,552,401 (Cullinan et al.) describes benzothiophene compounds as useful for the treatment of various medical indications associated with post-menopausal syndrome, and uterine fibroid disease, endometriosis, and aortal smooth muscle cell proliferation, the compounds being used in pharmaceutical formulations optionally containing estrogen or progestin. U.S. Pat. Nos. 5,646,137 and 5,591,753 (both issued to Black et al.) discloses methods of treating osteoporosis with formulations of raloxefine-type arylbenzothiophene compounds in conjunction with a progestin selected from medroxyprogesterone, norethindrone or norethynodrel, or pharmaceutically acceptable salts thereof. U.S Pat. No. 5,550,107 (Labrie) claims an invention comprising the treatment of breast or endometrial cancer with an antiestrogen together with at least one compound selected from the group of an androgen, a progestin, at least one inhibitor of sex steroid formation, expecially 17β-hydroxysteroid dehydrogenase and aromatase activity, at least one inhibitor of prolactin secretion, one inhibitor of growth hormone secretion and one inhibitor of ACTH secretion. U.S. Pat. No. 5,672,609 (Bryant et al.) discloses pyridine compounds useful in treating post menopausal syndrome and formulations therefore containing estrogen or progestin. U.S. Pat. No. 5,534,527 (Black et al.) teaches the use of aroylbenzothiophenes and estrogens in the inhibition of bone loss.

DESCRIPTION OF THE INVENTION

The present invention provides pharmaceutical formulations, and methods for using them, comprising compounds of formulas (I) and (II), below, in conjunction with estrogens, preferably in conjunction with one or more pharmaceutically acceptable carriers or excipients. Among the uses of the present formulations is alleviating the symptoms of post-menopausal syndrome in women, including peri-menopausal and post-menopausal symptoms. The present formulations and methods of treatment can be used to minimize undesirable side effects of estrogen treatment or therapy and may be used to minimize the amounts of estrogen(s) necessary for a particular regimen.

Compounds of the general structure type shown in formulas (I) and (II) are estrogen agonists/antagonists useful for the treatment of diseases associated with estrogen deficiency. The compounds of the present invention show strong binding to the estrogen receptor and are capable of antagonizing the effects of 17β-estradiol while showing little uterine stimulation when dosed alone.

The present invention includes, in conjunction with one or more estrogens, the use of compounds of formulas (I) or (II), below:

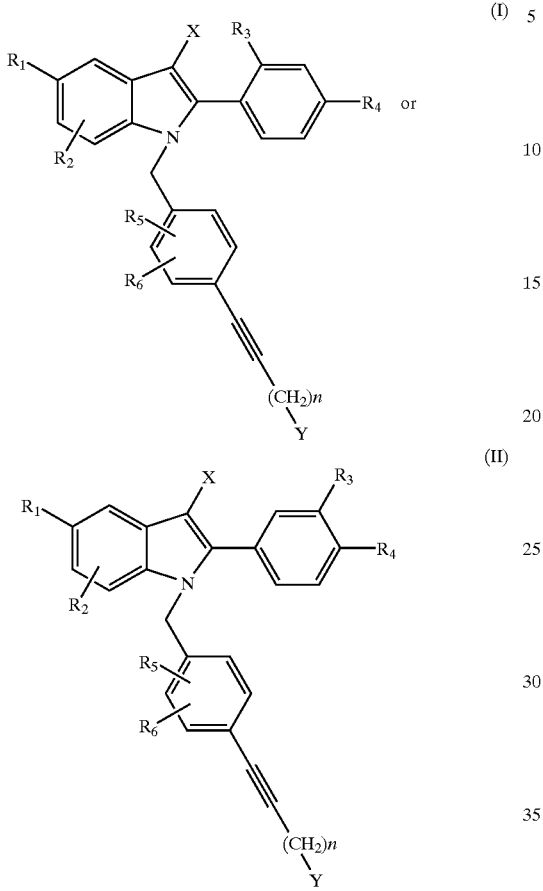

wherein:
R$_1$ is selected from H, OH or the C$_1$–C$_4$ esters or alkyl ethers thereof, or halogen;
R$_2$, R$_3$, R$_4$, R$_5$, and R$_6$ are independently selected from H, OH or the C$_1$–C$_4$ esters or alkyl ethers thereof, halogen, cyano, C$_1$–C$_6$ alkyl, or trifluoromethyl, with the proviso that, when R$_1$ is H, R$_2$ is not OH;
X is selected from H, C$_1$–C$_6$ alkyl, cyano, nitro, triflouromethyl, halogen;
n is 2 or 3;
Y is selected from:
  a) the moiety:

wherein R$_7$ and R$_8$ are independently selected from the group of H, C$_1$–C$_6$ alkyl, phenyl; or
  b) a five-membered saturated, unsaturated or partially unsaturated heterocycle containing up to two heteroatoms selected from the group consisting of —O—, —NH—, —N(C$_1$C$_4$ alkyl)—, —N=, and —S(O)$_m$—, wherein m is an integer of from 0–2, optionally substituted with 1–3 substituents independently selected from the group consisting of hydrogen, hydroxyl, halo, C$_1$–C$_4$ alkyl, trihalomethyl, C$_1$–C$_4$ alkoxy, trihalomethoxy, C$_1$–C$_4$ acyloxy, C$_1$–C$_4$ alkylthio, C$_1$–C$_4$ alkylsulfinyl, C$_1$–C$_4$ alkylsulfonyl, hydroxy (C$_1$–C$_4$)alkyl, —CO$_2$H—, —CN—, —CONHR$_1$—, —NH$_2$—, C$_1$–C$_4$ alkylamino, C$_1$–C$_4$ dialkylamino, —NHSO$_2$R$_1$—, —NHCOR$_1$—, —NO$_2$—, and phenyl optionally substituted with 1–3 (C$_1$–C$_4$)alkyl; or
  c) a six-membered saturated, unsaturated or partially unsaturated heterocycle containing up to two heteroatoms selected from the group consisting of —O—, —NH—, —N(C$_1$C$_4$ alkyl)—, —N=, and —S(O)$_m$—, wherein m is an integer of from 0–2, optionally substituted with 1–3 substituents independently selected from the group consisting of hydrogen, hydroxyl, halo, C$_1$–C$_4$ alkyl, trihalomethyl, C$_1$–C$_4$ alkoxy, trihalomethoxy, C$_1$–C$_4$ acyloxy, C$_1$–C$_4$ alkylthio, C$_1$–C$_4$ alkylsulfinyl, C$_1$–C$_4$ alkylsulfonyl, hydroxy (C$_1$–C$_4$)alkyl, —CO$_2$H—, —CN—, —CONHR$_1$—, —NH$_2$—, C$_1$–C$_4$ alkylamino, di(C$_1$–C$_4$)alkylamino, —NHSO$_2$R$_1$—, —NHCOR$_1$—, —NO$_2$, and phenyl optionally substituted with 1–3 (C$_1$–C$_4$)alkyl; or
  d) a seven-membered saturated, unsaturated or partially unsaturated heterocycle containing up to two heteroatoms selected from the group consisting of —O—, —NH—, —N(C$_1$C$_4$ alkyl)—, —N=, and —S(O)$_m$—, wherein m is an integer of from 0–2, optionally substituted with 1–3 substituents independently selected from the group consisting of hydrogen, hydroxyl, halo, C$_1$–C$_4$ alkyl, trihalomethyl, C$_1$–C$_4$ alkoxy, trihalomethoxy, C$_1$–C$_4$ acyloxy, C$_1$–C$_4$ alkylthio, C$_1$–C$_4$ alkylsulfinyl, C$_1$–C$_4$ alkylsulfonyl, hydroxy (C$_1$–C$_4$)alkyl, —CO$_2$H—, —CN—, —CONHR$_1$—, —NH$_2$—, C$_1$–C$_4$ alkylamino, di(C$_1$–C$_4$)alkylamino, —NHSO$_2$R$_1$—, —NHCOR$_1$—, —NO$_2$, and phenyl optionally substituted with 1–3 (C$_1$–C$_4$)alkyl; or
  e) a bicyclic heterocycle containing from 6–12 carbon atoms either bridged or fused and containing up to two heteroatoms selected from the group consisting of —O—, —NH—, —N(C$_1$C$_4$ alkyl)—, and —S(O)$_m$—, wherein m is an integer of from 0–2, optionally substituted with 1–3 substituents independently selected from the group consisting of hydrogen, hydroxyl, halo, C$_1$–C$_4$ alkyl, trihalomethyl, C$_1$–C$_4$ alkoxy, trihalomethoxy, C$_1$–C$_4$ acyloxy, C$_1$–C$_4$ alkylthio, C$_1$–C$_4$ alkylsulfinyl, C$_1$–C$_4$ alkylsulfonyl, hydroxy (C$_1$–C$_4$)alkyl, —CO$_2$H—, —CN—, —CONHR$_1$—, —NH$_2$—, C$_1$–C$_4$ alkylamino, di(C$_1$–C$_4$)alkylamino, —NHSO$_2$R$_1$—, —NHCOR$_1$—, —NO$_2$, and phenyl optionally substituted with 1–3 (C$_1$–C$_4$)alkyl;
and the pharmaceutically acceptable salts thereof The more preferred formulations and methods of treatment of this invention are those having or utilizing, along with one or more pharmaceutical carriers or excipients:
  a) one or more estrogens; and
  b) one or more compounds selected from the general structures I or II, above, wherein:
    R$_1$ is selected from H, OH or the C$_1$–C$_4$ esters or alkyl ethers thereof, halogen;
    R$_2$, R$_3$, R$_4$, R$_5$, and R$_6$ are independently selected from H, OH or the C$_1$–C$_4$ esters or alkyl ethers thereof, halogen, cyano, C$_1$–C$_6$ alkyl, or trifluoromethyl, with the proviso that, when R$_1$ is H, R$_2$ is not OH;
    X is selected from H, C$_1$–C$_6$ alkyl, cyano, nitro, trifluoromethyl, halogen;
    Y is the moiety

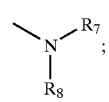

R$_7$ and R$_8$ are selected independently from H, C$_1$–C$_6$ alkyl, or combined by —(CH$_2$)p—, wherein p is an integer of from 2 to 6, so as to form a ring, the ring being optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$) alkyl, —$CO_2H$, —CN, —CONH($C_1$–C4)alkyl, —$NH_2$, $C_1$–$C_4$ alkylamino, $C_1$–$C_4$ dialkylamino, —$NHSO_2$($C_1$–$C_4$)alkyl, —NHCO($C_1$–C4), and —$NO_2$; or a pharmaceutically acceptable salt thereof.

The rings formed by a concatenated $R_7$ and $R_8$, mentioned above, may include, but are not limited to, aziridine, azetidine, pyrrolidine, piperidine, or hexamethyleneamine rings.

The most preferred of these compounds are those having the structural formulas I or II, above, wherein $R_1$ is OH; $R_2$–$R_6$ are as defined above; X is selected from the group of Cl, $NO_2$, CN, $CF_3$, or $CH_3$; and Y is the moiety

and $R_7$ and $R_8$ are concatenated together as —$(CH_2)p$—, wherein p is an integer of from 4 to 6, to form a ring optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —CONH($C_1$–$C_4$), —$NH_3$, $C_1$–$C_4$ alkylamino, $C_1$–$C_4$ dialkylamino, —$NHSO_2$ ($C_1$–$C_4$), —NHCO($C_1$–$C_4$), and —$NO_3$; and the pharmaceutically acceptable salts thereof.

It is further preferred that, when $R_7$ and $R_8$ are concatenated together as—$(CH_2)p$—, the ring so formed is optionally substituted with 1–3 substituents selected from a group containing $C_1$–$C_3$ alkyl, trifluoromethyl, halogen, hydrogen, phenyl, nitro, —CN.

The invention includes acceptable salt forms formed from the addition reaction with either inorganic or organic acids. Inorganic acids such as hydrochloric acid, hydrobromic acid, hydroiodic acid, sulfuric acid, phosphoric acid, nitric acid useful as well as organic acids such as acetic acid, propionic acid, citric acid, maleic acid, malic acid, tartaric acid, phthalic acid, succinic acid, methanesulfonic acid, toluenesulfonic acid, napthalenesulfonic acid, camphorsulfonic acid, benzenesulfonic acid are useful. It is known that compounds possessing a basic nitrogen can be complexed with many different acids (both protic and not protic) and usually it is preferred to administer a compound of this invention in the form of an acid addition salt.

Compounds of this invention can be synthesized in a general sense according to Scheme 1.

Scheme 1

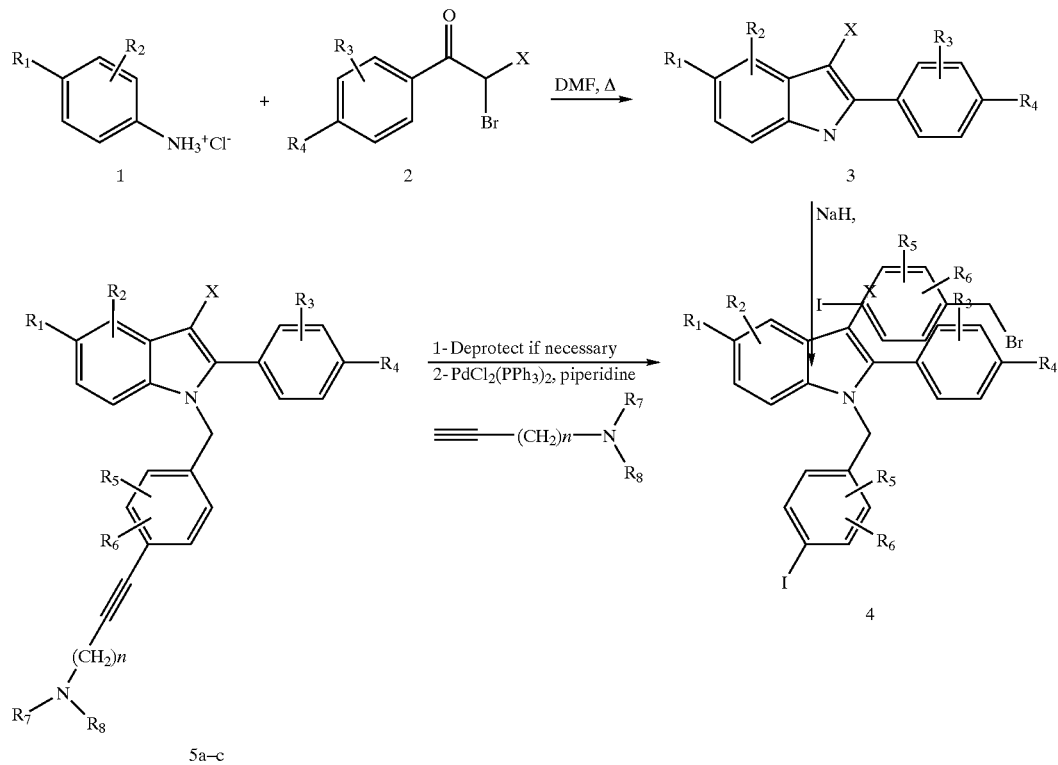

The initial indole synthesis may be accomplished by heating an appropriately substituted aniline (1) with an appropriately substituted alpha-bromophenylalkyl-phenone (2) in a suitably high boiling solvent such as DMF. The product is then alkylated with 4-iodobenzyl bromide to give the substituted indole (3). At this point, deprotection of phenols (if present) is done. Normally, the phenols are protected as benzyl ethers and can conveniently be cleaved with TMSI. The propargylamines can then be coupled to the phenyl iodide. The propargylamines are typically prepared from an alkynyl bromide or alkynyl tosylate by substitution with the appropriate amine. The substitution reaction is done in situ, without isolating the propargylamine. Compounds substituted at the 3-position with groups other then alkyl may be prepared by first preparing the indole substituted at the 3-position with —H. The indole can then be electrophilically halogenated, formylated, etc., to give other 3-substituted compounds.

The compounds of Formulas (I) and (II) are partial estrogen agonists and display high affinity for the estrogen receptor. Unlike many estrogens, however, these compounds do not cause increases in uterine wet weight. These compounds are antiestrogenic in the uterus and can completely antagonize the trophic effects of estrogen agonists in uterine tissue. These compounds are useful in treating or preventing mammal disease states or syndromes which are caused by or associated with an estrogen deficiency. This tissue selectivity allows their use for desirable estrogenic activity in certain tissues, such as bone, while limiting that activity in others, such as uterine tissue.

Estrogens useful in the formulations of this invention include estrone, estriol, equilin, estradiene, equilenin, ethinyl estradiol, 17β-estradiol, 17α-dihydroequilenin, 17β-dihydroequilenin (U.S. Pat. No. 2,834,712), 17α-dihydroequilin, 17β-dihydroequilin, menstranol and conjugated estrogenic hormones, such as those in Wyeth-Ayerst Laboratories' Premarin® products. Phytoestrogens, such as equol or enterolactone, may also be used in the present formulations and methods. A preferred embodiment of this invention comprises pharmaceutical compositions and methods of treatment utilizing conjugated estrogenic hormones, such as those in Wyeth-Ayerst Laboratories' Premarin® products, with one or more compounds of Formulas (I) or (III) listed herein. Esterified estrogens, such as those sold by Solvay Pharmaceuticals, Inc. under the Estratab® tradename, may also be used with the present formulations. Also preferred for use with the present invention are the salts of the applicable estrogens, most preferably the sodium salts. Examples of these preferred salts are Sodium estrone sulfate, Sodium equilin sulfate, Sodium 17alpha-dihydroequilin sulfate, Sodium 17alpha-estradiol sulfate, Sodium Delta8,9-dehydroestrone sulfate, Sodium equilenin sulfate, Sodium 17beta-dihydroequilin sulfate, Sodium 17alpha-dihydroequilenin sulfate, Sodium 17beta-estradiol sulfate, Sodium 17beta-dihydroequilenin sulfate, Estrone 3-sodium sulfate, Equilin 3-sodium sulfate, 17alpha-Dihydroequilin 3-sodium sulfate, 3beta-Hydroxy-estra-5(10), 7-dien-17-one 3-sodium sulfate, 5alpha-Pregnan-3beta-20R-diol 20-sodium sulfate, 5alpha-Pregnan-3beta, 16alpha-diol-20-one 3-sodium sulfate, delta (8,9)-Dehydroestrone 3-sodium sulfate, Estra-3beta, 17alpha-diol 3-sodium sulfate, 3beta-Hydroxy-estr-5(10)-en-17-one 3-sodium sulfate or 5alpha-Pregnan-3beta, 16alpha,20R-triol 3-sodium sulfate. Preferred salts of estrone include, but are not limited to, the sodium and piperate salts.

The present compounds of Formulas (I) and (II) are tissue selective compounds having the ability to behave like estrogen agonists, such as by lowering cholesterol and preventing bone loss, or like estrogen antagonists. Therefore, these compounds in the present formulations are useful for treating many maladies including osteoporosis, prostatic hypertrophy, infertility, breast cancer, endometrial hyperplasia, endometrial cancer, endometriosis, cystic glandular hyperplasia, uterine hyperplasia, cervical hyperplasia, benign prostatic hyperplasia, cardiovascular disease, contraception, Alzheimer's disease and melanoma. The formulations of this invention may also be used to treat bone loss resulting from secondary osteoporosis, including that categorized as endocrine in nature, including that resulting from glucocorticoid excess, hyperparathyroidism, hyperthyroidism, hypogonadism, hyperprolactinemia, and diabetes mellitus. The bone loss may also be the drug-induced, such as that resulting from heparin treatments, alcohol consumption, or the use of tobacco, barbiturates or corticosteroids. The drug-induced loss of bone may also stem from treatment with gonadotropin releasing hormone (GnRH or LHRH) or synthetic GnRH antagonists or agonists, such as the leuprolide acetate injectable sold by TAP Pharmaceuticals Inc. under the tradename LUPRON® or the goserelin acetate implant sold by Zeneca Pharmaceuticals under the Zoladex® tradename. Such bone loss may also result from immobilization of the individual, chronic renal failure, malabsorption syndrome, hepatic disease, chronic obstructive lung disease, rheumatoid arthritis, or sarcoidosis.

Additionally, these formulations can be used for hormone replacement therapy in post-menopausal women or in other estrogen deficiency states where estrogen supplementation would be beneficial. The symbiotic activity of the compounds and estrogen(s) of the present methods of treatment are particularly of interest in overcoming the unwanted consequences of estrogen therapy, such as breakthrough bleeding and/or excessive endometrial stimulation, which may lead to endometrial hyperplasia or endometriosis. These formulations, therefore, may be used in methods of treating or preventing excessive estrogenic uterine stimulation in a mammal.

The formulations of this invention may also be used in methods of treatment for bone loss, which may result from an imbalance in an individual's formation of new bone tissues and the resorption of older tissues, leading to a net loss of bone. Such bone depletion results in a range of individuals, particularly in post-menopausal women, women who have undergone hysterectomy/oophorectomy, those receiving or who have received extended corticosteroid therapies, those experiencing gonadal dysgenesis, and those suffering from Cushing's syndrome. Special needs for bone replacement can also be addressed using these formulations in individuals with bone fractures, defective bone structures, and those receiving bone-related surgeries and/or the implantation of prosthesis. In addition to those problems described above, these formulations can be used in treatments for osteoarthritis, Paget's disease, osteomalacia, osteohalisteresis, endometrial cancer, multiple myeloma and other forms of cancer having deleterious effects on bone tissues. Methods of treating the maladies listed herein are understood to comprise administering to an individual in need of such treatment a pharmaceutically effective amount of one or more of the compounds of Formulas (I) and (II), or a pharmaceutically acceptable salt thereof, in conjunction with a therapeutically desirable amount of an estrogen. This invention also includes pharmaceutical compositions utilizing one or more of the present compounds, and/or the pharmaceutically acceptable salts thereof, along with one or more pharmaceutically acceptable carriers, excipients, etc.

Estrogens regulate a number of physiological processes. The primary target tissues for estrogens include the reproductive tract (ovary; uterus; vagina), mammary tissue, skeleton, cardiovascular system and the central nervous system (CNS). The reduction in circulating estrogens results in a number of changes. There is a cessation in reproductive function with an associated amenorrhea, uterine atrophy, and increase in vaginal dryness (lack of keratinization). Mammary tissue becomes relatively quiescent. There is an increase in the rate of loss of bone mass (2–7%) compared to the normal 0.5–1.0%/year that is seen in all individuals over the age of 35. A change in lipid profile occurs with increases in Low Density Lipoprotein (LDL) and decreases in High Density Lipoprotein (HDL) commonly measured and an associated increased risk of a cardiovascular event (heart attack, stroke). Changes in the central nervous system include an increase in vasomotor symptoms (hot flush) and potentially changes in cognition and memory.

Estrogen replacement therapy (ERT) normalizes some of these changes, particularly those associated with the cardiovascular system (reduced LDL, increased HDL, reduced risk of heart attack), the skeleton (maintenance of bone mass, reduced fracture risk), and central nervous system (reduction in frequency and severity of the hot flush). While the reproductive tract responds, it is not all positive. On the positive side, vaginal dryness is alleviated. However, negative uterine responses include hypertrophy and hyperplasia, along with some menstrual-like bleeding. The breast is also affected and there are data correlating exogenous estrogen therapy with an increased risk of breast cancer.

Currently, women with intact uteri are not generally prescribed estrogens alone, but estrogens in combination with a progestin to reduce uterine stimulation. While the risks of endometrial cancer are reduced to non-hormone treated levels, the other side effects of progestins reduce compliance in women on hormone replacement.

The tissue selective estrogen (TSE) compounds of this invention provide positive skeletal and cardiovascular affects similar to estrogens, without the negative effects associated with the uterus and breast. The combinations of TSEs and estrogens derive the positive effects of estrogens on the CNS, bone and cardiovascular, with the combination providing complimentary or additive effects on the bone and cardiovascular systems. The major variable is the TSEs ability to block estrogenic influence on the uterus and breast, which are the two major negative effects of unopposed estrogens.

It is understood that the dosage, regimen and mode of administration of these compounds of Formulas (I) and (II) will vary according to the malady and the individual being treated and will be subjected to the judgment of the medical practitioner involved. It is preferred that the administration of one or more of the compounds herein begins at a low dose and be increased until the desired effects are achieved. Similarly, it will be understood that the dosage(s) of the estrogen(s) utilized in the present formulations will be selected according to conventional methods. It is most preferred that the dosage will be monitored to achieve the desired result with the minimum of estrogen(s) necessary.

Effective administration of these compounds of Formulas (I) and (II) may be given at a dose of from about 0.01 mg/day to about 1,000 mg/day. Preferably, administration will be from about 1 mg/day to about 600 mg/day in a single dose or in two or more divided doses. Most preferably a daily dose of between about 1 mg/day and about 150 mg/day will be administered. Such doses may be administered in any manner useful in directing the active compounds herein to the recipient, including orally, parenterally (including intravenous, intraperitoneal and subcutaneous injections, implants, etc.), intravaginally and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of Formulas (I) and (II) may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It will be understood that the estrogen of this invention will be administered in the dosages of conventional regimens, according to the recipient's tolerance and the particular treatment or maintenance schedule intended. The compounds of Formulas (I) and (II) herein will be administered in an amount necessary to agonize or antagonize the estrogen(s) of the formulation's activity to the level desired. When conjugated estrogens, USP, are used, it is preferred that the daily doseage is from 0.1 mg to 5.0 mg, more preferably between about 0.3 mg and about 2.5 mg, most preferably between about 0.3 and about 1.25 mg/day. For mestranol or ethynyl estradiol a daily dosage may be from about 1 pg to about 0.15 mg/day and a dosage of from about 1 $\mu$g to about 0.3 mg/day may be used for ethynyl estradiol, preferably between about 2 $\mu$g to about 0.15 mg/day of ethynyl estradiol.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository, creams, gels, etc. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached; precise dosages for oral, parenteral, transdermal, rectal or vaginal suppositories, nasal, or intrabronchial and other administrations will be determined by the administering physician based on experience with the individual subject treated. Preferably, the pharmaceutical composition is in unit dosage form, e.g. as tablets or capsules. In such form, the composition is subdivided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The compound(s) of Formulas (I) and (II) and the estrogen(s) of the present formulations may be administered in separate dosage units, such as separate pills, tablets, powders, etc., or combined into one formulation. When optimum dosages for the compounds of Formulas (I) and (II) and the estrogens of these formulations have been determined, it may preferable to incorporate both into a single formulation for ease of administration. It is also understood that the formulations herein may or may not include other pharmaceutically active components.

Solvents used for the reactions described herein were anhydrous Aldrich Sure Seal™ without further purification. Reagents were typically Aldrich and used without further purification. All reactions were carried out under a nitrogen atmosphere. Chromatography was performed using 230–400 mesh silica gel (Merck Grade 60, Aldrich Chemical Company). Thin layer chromatography was performed with Silica Gel 60 $F_{254}$ plates from EM Science. $^1$H NMR spectra were obtained on a Bruker AM-400 instrument in DMSO and chemical shifts reported in ppm. Melting points were determined on a Thomas-Hoover apparatus and are uncorrected. IR spectra were recorded on a Perkin-Elmer diffraction grating or Perkin-Elmer 784 spectrophotometers. Mass spectra were recorded on a Kratos MS 50 or Finnigan 8230 mass spectrometers. Elemental analyses were obtained with a Perkin-Elmer 2400 elemental analyzer. Analysis values for compounds with CHN analysis reported were within 0.4% of theoretical values.

The present invention is further illustrated by the following non-limiting examples.

EXAMPLE 1

5-Benzyloxy-2-(4-benzyloxy-phenyl)-3-methyl-1H-indole

A flask was charged with 4-benzyloxyaniline (45 g, 0.23 mol), 4'-benzyloxy-2-bromophenylpropiophenone (21 g, 0.066 mol), and DMF (50 mL). The reaction was heated at reflux for 30 minutes and then cooled to rt and then partitioned between EtOAc (250 mL) and 1N HCl (aq) (100 mL). The EtOAc was washed with $NaHCO_3$ (aq) and brine, dried over $MgSO_4$. The solution was concentrated and the residue taken up in $CH_2Cl_2$ and hexanes added to precipitate out 25 g of a crude solid. The solid was dissolved in $CH_2Cl_2$ and evaporated onto silica gel and chromatographed using $CH_2Cl_2$/Hexane (1:5) to yield 9.2 g of a tan solid (33%): Mpt=150–152° C.; $^1$H NMR (DMSO) 10.88 (s, 1 H), 7.56 (d, 2 H, J=8.8 Hz), 7.48 (d, 4 H, J=7.9 Hz), 7.42–7.29 (m, 6 H), 7.21 (d, 1 H, J=7.0 Hz), 7.13 (d, 2 H, J=8.8 Hz), 7.08 (d, 1 H, J=2.2 Hz), 6.94 (dd, 1 H, J=8.8, 2.4 Hz), 5.16 (s, 2 H), 5.11 (s, 2 H), 2.33 (s, 3 H); IR (KBr) 3470, 2880, 2820, 1620 $cm^{-1}$; MS eI m/z 419.

EXAMPLE 2

5-Benzyloxy-2-(4-benzyloxy-phenyl)-3-methyl)-1-ylmethyl-(4-phenyliodide)-indole

A solution of 4 (3.0 g, 7.4 mmol) in DMF (25 mL) was treated with NaH (60% dispersion, 0.21 g, 8.9 mmol) and stirred at rt for 15 minutes. 4-iodobromobenzyl bromide (2.2 g, 7.4 mmol) was added and the reaction was stirred for 1 hour. The reaction mixture was poured into water and extracted with EtOAc, dried over $MgSO_4$ and concentrated. Trituration of the crude product with ether afforded 2.2 g of the product as a white solid: Mpt=153–156° C.; $^1$H NMR (DMSO) 7.54 (d, 2 H, J=8.6 Hz), 7.52–7.45 (m, 4 H), 7.37–7.29 (m, 6 H), 7.27 (d, 2 H, J=8.8 Hz), 7.17 (d, 1 H, J=9.0 Hz), 7.13 (d, 1 H, J=2.2 Hz), 7.10 (d, 2 H, J=8.8 Hz), 6.81 (dd, 1 H, J=8.8, 2.4 Hz), 6.60 (d, 2 H, J=8.3 Hz), 5.18 (s, 2 H), 5.12 (s, 2 H), 5.11 (s, 2 H), 2.15 (s, 3 H); MS eI m/z 635.

EXAMPLE 3

2-(4-Hydroxyphenyl)-3-methyl-1-ylmethyl-(4-phenyliodide)-indole-5-ol

A solution of 4 (2.2 g, 3.5 mmol) in $CHCl_3$ was treated with Iodotrimethylsilane (1.04 mL, 7.0 mmol) and the reaction was heated to reflux. After 2 h, an additional 3 eq of Iodotrimethylsilane was added and the reaction was stirred at rt for 18 h. The reaction was quenched by adding MeOH (5 mL). The organic layer was washed with an aqueous 10% solution of $Na_2SO_3$, HCl (1M) and dried over $MgSO_4$. The solution was concentrated and chromatographed on silica gel EtOAc/hexane (3:7) to yield 4a as a foam (1.2 g): $^1$H NMR 9.65 (s, 1 H), 8.71 (s, 1 H), 7.54 (d, 2 H, J=8.3 Hz), 7.12 (d, 2 H, J=8.3 Hz), 7.02 (d, 1 H, J=8.6 Hz), 6.84–6.80 (m, 3 H), 6.61 (d, 2 H, J=8.3 Hz), 6.57 (dd, 1 H, J=6.4 Hz), 5.12 (s, 2 H), 2.09 (s, 3 H); MS eI m/z 455.

General Procedure For Indole Propargylamine Preparation

The title compounds of Examples 4–6 were produced using a solution containing a 10 fold molar excess of a secondary amine in DMF cooled to 0C° C. and treated with propargyl bromide (3 eq, 80% solution in toluene). After 1 h at 0° C., the reactions were allowed to rt for 1 h. The indole iodide (4a, 1 eq) was added followed by Cu(I)I (0.1 eq) and $Pd(PPh_3)_2Cl_2$ (0.035 eq). The reaction mixture was then stirred 16–48 h and worked up by pouring into water and extracting into EtOAc. The EtOAc is concentrated and chromatographed on silica gel using EtOAc/hexane as eluting system.

EXAMPLE 4

2-(4-Hydroxy-phenyl)-3-methyl-1-[4-(3-N,N-dimethyl-1-yl-prop-1-ynyl)-benzyl]-1H-indol-5-ol Mp=173–176° C.; $^1$H NMR (DMSO) 9.64 (s, 1 H), 8.70 (s, 1 H), 7.25 (d, 2 H, J=8.1 Hz), 7.12 (d, 2 H, J=8.3 Hz), 7.03 (d, 1 H, J=8.6 Hz), 6.83–6.78 (m, 5 H), 6.57 (dd, 1 H, J=8.8, 2.4 Hz), 5.17 (s, 2 H), 3.39 (s, 2 H), 2.19 (s, 6 H), 2.10 (s, 3 H); IR (KBr) 3390, 1490 $cm^{-1}$; MS esI 411 (M+H$^+$).

EXAMPLE 5

2-(4-Hydroxy-phenyl)-3-methyl-1-[4-(3-piperidin-1-yl-prop-1-vinyl)-benzyl]-1H-indol-5-ol Mp=118–123° C.; $^1$H NMR (DMSO) 9.65 (s, 1 H), 8.71 (s, 1 H), 7.24 (d, 2 H, J=8.1 Hz), 7.12 (d, 2 H, J=8.6 Hz), 7.02 (d, 1 H, J=8.6 Hz), 6.83–6.80 (m, 5 H), 6.57 (dd, 1 H, J=8.6, 2.2 Hz), 5.17 (s, 2 H), 3.39 (s, 2 H), 2.41 (m, 4 H), 2.10 (s, 3 H), 1.48 (p, 4 H, J=5.7 Hz), 1.36–1.33 (m, 2 H); IR (KBr) 3400, 2920, 1620, 1420 $cm^{-1}$; MS EI m/z 450; CHN calc'd for $C_{30}H_{30}N_2O_2$+0.25 $H_2O$

EXAMPLE 6

2-(4-Hydroxy-phenyl)-3-methyl-1-[4-(3-pyrrolidin-1-yl-prop-1-ynyl)-benzyl]-1H-indol-5-ol (5c)

Mp=174–176° C.; 1H NMR (DMSO) 9.64 (s, 1 H), 8.70 (s, 1 H), 7.23 (d, 2 H, J=8.3 Hz), 7.11 (d, 2 H, J=8.6 Hz), 7.02 (d, 1 H, J=8.8 Hz), 6.84 (m, 5 H), 6.57 (dd, 1 H, J=8.6, 2.2 Hz), 5.17 (s, 2 H), 3.53 (s, 2 H), 2.53–2.51 (m, 4 H), 2.09 (s, 3 H), 1.69–1.66 (m, 4 H); IR (KBr) 3400, 2920, 2900, 1620 $cm^{-1}$; MS eI m/z 436; CHN calcd for $C_{29}H_{28}N_2O_2$+0.7 $H_2O$.

In Vitro Estrogen Receptor Binding Assay

Receptor Preparation

CHO cells overexpressing the estrogen receptor were grown in 150 $mm^2$ dishes in DMEM+10% dextran coated charcoal, stripped fetal bovine serum. The plates were washed twice with PBS and once with 10 mM Tris-HCl, pH 7.4, 1 mM EDTA. Cells were harvested by scraping the surface and then the cell suspension was placed on ice. Cells were disrupted with a hand-held motorized tissue grinder using two, 10-second bursts. The crude preparation was centrifuged at 12,000 g for 20 minutes followed by a 60 minute spin at 100,000 g to produce a ribosome free cytosol. The cytosol was then frozen and stored at –80° C. Protein concentration of the cytosol was estimated using the BCA assay with reference standard protein.

Binding Assay Conditions

The competition assay was performed in a 96-well plate (polystyrene*) which binds <2.0% of the total input [$^3$H]-17β-estradiol and each data point was gathered in triplicate. 100 uG/100 uL of the receptor preparation was aliquoted per well. A saturating dose of 2.5 nM [$^3$H]17β-estradiol+ competitor (or buffer) in a 50 uL volume was added in the preliminary competition when 100× and 500× competitor were evaluated, only 0.8 nM [$^3$H]17β-estradiol was used. The plate was incubated at room temperature for 2.5 h. At the end of this incubation period 150 uL of ice-cold dextran coated charcoal (5% activated charcoal coated with 0.05% 69K dextran) was added to each well and the plate was immediately centrifuged at 99 g for 5 minutes at 4° C. 200 uL of the supernatant solution was then removed for scintillation counting. Samples were counted to 2% or 10 minutes, whichever occurs first. Because polystyrene absorbs a small amount of [$^3$H]17β-estradiol, wells containing radioactivity and cytosol, but not processed with charcoal were included to quantitate amounts of available isotope. Also, wells containing radioactivity but no cytosol were processed with charcoal to estimate unremovable DPM of [$^3$H]17β-estradiol. Corning #25880-96, 96-well plates were used because they have proven to bind the least amount of estradiol.

Analysis of Results

Counts per minute (CPM) of radioactivity were automatically converted to disintegrated per minute (DPM) by the Beckman LS 7500 Scintillation Counter using a set of quenched standards to generate a H# for each sample. To calculate the % of estradiol binding in the presence of 100 or fold 500 fold competitor the following formula was applied:

((DPM sample–DPM not removed by charcoal/(DPM estradiol– DPM not removed by charcoal))×100%=% of estradiol binding For the generation of $IC_{50}$ curves, % binding is plotted vs compound. $IC_{50}$'s are generated for compounds that show >30% competition at 500× competitor concentration. For a description of these methods, see Hulme, E. C., ed. 1992. Receptor-Ligand Interactions: A Practical Approach. IRL Press, New York.(see especially chapter 8).

Estrogen Receptor Affinity (reported as RBA: 17β-estradiol=100)

| Compound  | RBA |
|-----------|-----|
| Raloxifene | 400 |
| Tamoxifen  | 1.8 |
| Example 4  | 53  |
| Example 5  | 23  |

Ishikawa Cell Alkaline Phosphatase Assay

Cell Maintenance and Treatment:

Ishikawa cells were maintained in DMEM/F12 (50%:50%) containing phenol red+10% fetal bovine serum and the medium was supplemented with 2 mM Glutamax, 1% Pen/Strap and 1 mM sodium pyruvate. Five days prior to the beginning of each experiment (treatment of cells) the medium was changed to phenol red-free DMEM/F12+10% dextran coated charcoal stripped serum. On the day before treatment, cells were harvested using 0.5% trypsin/EDTA and plated at a density of $5 \times 10^4$ cells/well in 96-well tissue culture plates. Test compounds were dosed at $10^{-6}$, $10^{-7}$ and $10^{-8}$ M in addition to $10^{-6}$ M (compound)+$10^{-9}$ M 17β-estradiol to evaluate the ability of the compounds to function as antiestrogens. Cells were treated for 48 h prior to assay. Each 96-well plate contained a 17β-estradiol control. Sample population for at each dose was n=8.

Alkaline Phosphatase Assay:

At the end of 48 h the media is aspirated and cells are washed three times with phosphate buffered saline (PBS). 50 μL of lysis buffer (0.1 M Tris-HCl, pH 9.8, 0.2% Triton X-100) is added to each well. Plates are placed at −80° C. for a minimum of 15 minutes. Plates are thawed at 37° C. followed by the addition of 150 μL of 0.1 M Tris-HCl, pH 9.8, containing 4 mM para-nitrophenylphosphate (pNPP) to each well (final concentration, 3 mM pNPP).

Absorbance and slope calculations were made using the KineticCalc Application program (Bio-Tek Instruments, Inc., Winooski, VT.). Results are expressed as the mean +/−S.D. of the rate of enzyme reaction (slope) averaged over the linear portion of the kinetic reaction curve (optical density readings every 5 minutes for 30 minutes absorbance reading). Results for compounds are summarized as percent of response related to 1 nM 17β-estradiol.

Various compounds were assayed for estrogenic activity by the alkaline phosphatase method and corresponding ED50 values (95% C.I.) were calculated. The four listed in the following were used as as reference standards:

| 17β-estradiol | 0.03 nM |
|---------------|---------|
| 17α-estradiol | 1.42 nM |
| estriol       | 0.13 nM |
| estrone       | 0.36 nM |

A description of these methods is described by Holinka, C. F., Hata, H., Kuramoto, H. and Gurpide, E. (1986) Effects of steroid hormones and antisteroids on alkaline phosphatase activity in human endometrial cancer cells (Ishikawa Line). Cancer Research, 46:2771–2774, and by Littlefield, B. A., Gurpide, E., Markiewicz, L., McKinley, B. and Hochberg, R. B. (1990) A simple and sensitive microtiter plate estrogen bioassay based on stimulation alkaline phosphatase in Ishikawa cells; Estrogen action of D5 adrenal steroids. Endocrinology, 6:2757–2762.

Ishikawa Alkaline Phosphatase Assay

| Compound | % Activation | % Activation (Compound + 1 nM 17β-estradiol) |
|----------|--------------|----------------------------------------------|
| 17#-estradiol | 100% | N/A |
| tamoxifen | 0% | 45% |
| raloxifen | 5% | 5% |
| Example 4 | 34% | 34% |
| Example 5 | 27% | 23% |

2×VIT ERE Transfection Assay

Cell Maintenance and Treatment

Chinese Hamster Ovary cells (CHO) which had been stably transfected with the human estrogen receptor were maintained in DMEM+10% fetal bovine serum (FBS). 48 h prior to treatment the growth medium was replaced with DMEM lacking phenol red+10% dextran coated charcoal stripped FBS (treatment medium). Cells were plated at a density of 5000 cells/well in 96-well plates containing 200 μL of medium/well.

Calcium Phoshate Transfection

Reporter DNA (Promega plasmid pGL2 containing two tandem copies of the vitellogenin ERE in front of the minimal thymidine kinase promoter driving the luciferase gene) was combined with the B-galactosidase expression plasmid pCH 110 (Pharmacia) and carrier DNA (pTZ18U) in the following ratio:

10 uG of reporter DNA 5 uG of pCH110DNA 5 uG of pTZ18U 20 uG of DNA/1 mL of transfection solution The DNA (20 uG) was dissolved in 500 uL of 250 mM sterile $CaCl_2$ and added dropwise to 500 uL of 2×HeBS (0.28 M NaCl, 50 mM HEPES, 1.5 mM $Na_2HPO_4$, pH 7.05) and incubated at room temperature for 20 minutes. 20 uL of this mixture was added to each well of cells and remained on the cells for 16 h. At the end of this incubation the precipitate was removed, the cells were washed with media, fresh treatment media was replaced and the cells were treated with either vehicle, 1 nM 17β-estradiol, 1 uM compound or 1 uM compound+1 nM 17β-estradiol (tests for estrogen antagonism). Each treatment condition was performed on 8 wells (n=8) which were incubated for 24 h prior to the luciferase assay.

Luciferase Assay

After 24 h exposure to compounds, the media was removed and each well washed with 2× with 125 uL of PBS lacking $Mg^{++}$ and $Ca^{++}$. After removing the PBS, 25 uL of Promega lysis buffer was added to each well and allowed to stand at room temperature for 15 min, followed by 15 min at −80° C. and 15 min at 37° C. 20 uL of lysate was transferred to an opaque 96 well plate for luciferase activity evaluation and the remaining lysate (5 uL) was used for the B-galactosidase activity evaluation (normalize transfection). The luciferan substrate (Promega) was added in 100 uL aliquots to each well automatically by the luminometer and the light produced (relative light units) was read 10 seconds after addition.

Infection Luciferase Assay

| Compound | % Activation | % Activation with 1 nM 17β-estradiol |
|---|---|---|
| 17β-estradiol | 100% | N/A |
| tamoxifen | 0% | 10% |
| raloxifene | 0% | 0% |
| Example 4 | 34% | 34% |
| Example 5 | 17% | 19% |

B-Galactosidase Assay

To the remaining 5 uL of lysate 45 uL of PBS was added. Then 50 uL of Promega B-galactosidase 2× assay buffer was added, mixed well and incubated at 37° C. for 1 hour. A plate containing a standard curve (0.1 to 1.5 milliunits in triplicate) was set up for each experimental run. The plates were analyzed on a Molecular Devices spectrophotometric plate reader at 410 nm. The optical densities for the unknown were converted to milliunits of activity by mathematical extrapolation from the standard curve.

Analysis of Results

The luciferase data was generated as relative light units (RLUs) accumulated during a 10 second measurement and automatically transferred to a JMP (SAS Inc) file where background RLUs were subtracted. The B-galactosidase values were automatically imported into the file and these values were divided into the RLUs to normalize the data. The mean and standard deviations were determined from a n=8 for each treatment. Compounds activity was compared to 17β-estradiol for each plate. Percentage of activity as compared to 17β-estradiol was calculated using the formula %=((Estradiol-control)/(compound value))×100. These techniques are described by Tzukerman, M. T., Esty, A., Santiso-Mere, D., Danielian, P., Parker, M. G., Stein, R. B., Pike, J. W. and McDonnel, D. P. (1994). Human estrogen receptor transactivational capacity was determined by both cellular and promoter context and mediated by two functionally distinct intramolecular regions (see Molecular Endocrinology, 8:21–30).

Rat Uterotrophic/Antiuterotrophic Bioassay

The estrogenic and antiestrogenic properties of the compounds were determined in an immature rat uterotrophic assay (4 day) that (as described previously by L. J. Black and R. L. Goode, Life Sciences, 26, 1453 (1980)). Immature Sprague-Dawley rats (female, 18 days old) were tested in groups of six. The animals were treated by daily ip injection with 10 uG compound, 100 uG compound, (100 uG compound+1 uG 17β-estradiol) to check antiestrogenicity, and 1 uG 17β-estradiol, with 50% DMSO/50% saline as the injection vehicle. On day 4 the animals were sacrificed by $CO_2$ asphyxiation and their uteri were removed and stripped of excess lipid, any fluid removed and the wet weight determined. A small section of one horn was submitted for histology and the remainder used to isolate total RNA in order to evaluate complement component 3 gene expression.

3 Day Ovariectomized Rat Model

| Compound | 10 μG | 100 μG | 100 μG + 1 μG 17β-estradiol |
|---|---|---|---|
| Tamoxifen | 69.6 mg | 71.4 mg | |
| Raloxifen | 47.5 | 43.2 | |
| control = 42.7 mg | | 1 μG 17β-estradiol = 98.2 | |
| Example 4 | 56.0 mg | 84.0 mg | 77.6 mg |
| control = 32.1 mg | | 1 μG 17β-estradiol = 90.2 mg | |
| Example 5 | 55.6 mg | 71.3 mg | 66.8 mg |
| control = 21.7 mg | | 1 μg 17β-estradiol = 82.8 mg | |

What is claimed:

1. A method of preventing excessive estrogenic uterine stimulation in a mammal, the method comprising administering to a mammal in need thereof an estrogen and an effective amount of a compound having the structure:

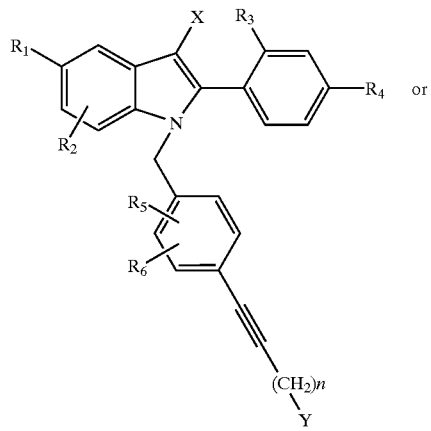

or

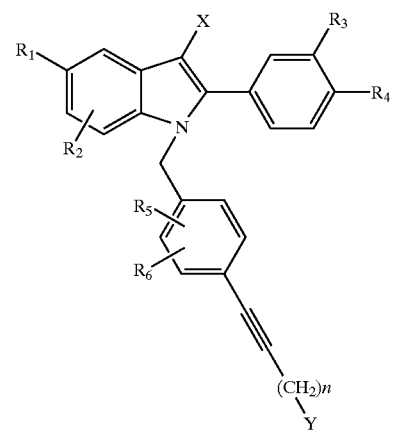

wherein:
$R_1$ is selected from H, OH or the $C^1$–$C_4$ esters or alkyl ethers thereof, or halogen;
$R_2$, $R_3$, $R_4$, $R_5$, and $R_6$ are independently selected from H, OH or the $C_1$–$C_4$ esters or alkyl ethers thereof, halogen, cyano, $C_1$–$C_6$ alkyl, or trifluoromethyl, with the proviso that, when $R_1$ is H, $R_2$ is not OH;
X is selected from H, $C_1$–$C_6$ alkyl, cyano, nitro, trifluoromethyl, or halogen;
n is 2 or 3;
Y is the moiety:

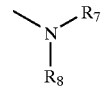

$R_7$ and $R_8$ are selected independently from H, $C_1$–$C_6$ alkyl, or combined by —$(CH_2)p$—, wherein p is an integer of from 2 to 6, so as to form a ring, the ring being optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —CONH($C_1$–$C_4$)alkyl, —$NH_3$, $C_1$–$C_4$ alkylamino, di($C_1$ –C4)alkylamino, —$NHSO_2$($C_1$–C4) alkyl, —NHCO($C_1$–$C_4$)alkyl, and —$NO_2$;

or a pharmaceutically acceptable salt thereof.

2. A method of preventing excessive estrogenic uterine stimulation in a mammal in need thereof, comprising administering to said mammal an effective amount of a combination of conjugated estrogens and 2-(4-hydroxy-phenyl)-3-methyl-1-[4-(3-piperidin-1-yl-prop-1-ynyl)-benzyl]-1H-indol-5-ol, or a pharmaceutically acceptable salt thereof.

* * * * *